United States Patent
Tatum et al.

[11] Patent Number: 6,022,326
[45] Date of Patent: Feb. 8, 2000

[54] DEVICE AND METHOD FOR AUTOMATIC COLLECTION OF WHOLE SALIVA

[75] Inventors: G. Roger Tatum; David J. Smith; Charles Woodruff, Jr.; Connie Chang, all of Rancho Cucamonga, Calif.

[73] Assignee: Lifepoint, Inc., Rancho Cucamonga, Calif.

[21] Appl. No.: 09/183,295

[22] Filed: Oct. 30, 1998

[51] Int. Cl.[7] ........................................ A61B 5/00
[52] U.S. Cl. .................... 600/573; 600/578; 433/91; 433/96
[58] Field of Search .................. 600/573, 576, 600/578, 579, 582, 584; 433/91, 92, 96

[56] References Cited

U.S. PATENT DOCUMENTS

| | | | |
|---|---|---|---|
| 3,731,675 | 5/1973 | Kelly | 128/62 A |
| 4,114,605 | 9/1978 | McGhee et al. | 128/2 F |
| 4,417,874 | 11/1983 | Andersson et al. | 433/96 |
| 4,580,577 | 4/1986 | O'Brien et al. | 128/760 |
| 4,635,488 | 1/1987 | Kremer | 73/864.72 |
| 4,678,238 | 7/1987 | Kleinberg et al. | 4/258 |
| 4,817,632 | 4/1989 | Schramm | 128/760 |
| 4,834,110 | 5/1989 | Richard | 128/760 |
| 5,022,409 | 6/1991 | Goldstein et al. | 128/760 |
| 5,050,616 | 9/1991 | Wolff et al. | 128/760 |
| 5,103,836 | 4/1992 | Goldstein et al. | 128/760 |
| 5,112,758 | 5/1992 | Fellman et al. | 436/8 |
| 5,183,740 | 2/1993 | Ligler et al. | 435/7.32 |
| 5,195,952 | 3/1993 | Solnit et al. | 433/91 |
| 5,260,031 | 11/1993 | Seymour | 422/101 |
| 5,268,148 | 12/1993 | Seymour | 422/101 |
| 5,334,502 | 8/1994 | Sangha | 433/7.21 |
| 5,339,829 | 8/1994 | Thieme et al. | 128/760 |
| 5,354,654 | 10/1994 | Ligler et al. | 435/5 |
| 5,376,337 | 12/1994 | Seymour | 422/101 |
| 5,380,492 | 1/1995 | Seymour | 422/101 |
| 5,393,496 | 2/1995 | Seymour | 422/101 |
| 5,464,397 | 11/1995 | Powers, Jr. | 433/95 |
| 5,479,937 | 1/1996 | Thieme et al. | 128/760 |
| 5,494,646 | 2/1996 | Seymour | 422/101 |
| 5,573,009 | 11/1996 | Thieme et al. | 128/760 |
| 5,690,487 | 11/1997 | Whitehouse et al. | 433/91 |
| 5,704,785 | 1/1998 | Young | 433/91 |
| 5,714,341 | 2/1998 | Thieme et al. | 435/22 |
| 5,738,519 | 4/1998 | Tenniswood | 433/92 |
| 5,743,736 | 4/1998 | Folko et al. | 433/96 |
| 5,813,856 | 9/1998 | Lee | 433/91 |
| 5,931,671 | 8/1999 | Hoffman | 433/91 |

FOREIGN PATENT DOCUMENTS

| | | |
|---|---|---|
| 2077528 | 4/1994 | Canada . |
| 2077529 | 4/1994 | Canada . |
| 0 056 241 B1 | 4/1986 | European Pat. Off. . |
| 0 520 408 A2 | 12/1992 | European Pat. Off. . |
| 934404 | 6/1993 | South Africa . |
| WO 94/07419 | 4/1994 | WIPO . |
| WO 94/18891 | 9/1994 | WIPO . |
| WO 94/18892 | 9/1994 | WIPO . |
| WO 97/12681 | 4/1997 | WIPO . |
| WO 97/10836 | 5/1997 | WIPO . |
| WO 97/20502 | 6/1997 | WIPO . |

*Primary Examiner*—Cary O'Connor
*Assistant Examiner*—Charles Marmor, II
*Attorney, Agent, or Firm*—Lyon & Lyon LLP

[57] ABSTRACT

A method and device for automatic or semi-automatic collection of saliva has a mouthpiece on a wand. The wand is connected to an interface section via a flexible conduit. Saliva is transported by aspiration into the device. Bulk air is removed and saliva is collected in a collection chamber. For collection of volatile components, air flow, vacuum, conduit diameter and length, and collection times are controlled and limited, to reduce loss of volatile components.

32 Claims, 3 Drawing Sheets

DEVICE AND METHOD FOR AUTOMATIC COLLECTION OF WHOLE SALIVA

BACKGROUND OF THE INVENTION

The field of the present invention is the automatic collection of oral fluids for subsequent analytical testing. Oral fluids means liquid secretions of the salivary glands and cervicular fluid mixed with other particles found naturally in the mouth including bacteria, leukocytes, sloughed epithelial cells, and particles of food and dental plaque (Soderling, E. "Practical Aspects of Salivary Analyses," in Tenovuo, J. O. (ed.), *Human Saliva: Clinical Chemistry and Microbiology*, Vol. 1. Boca Raton, Fla.: CRC Press (1988), Ch. 1, p. 2). The terms oral fluids, whole saliva, and saliva are used synonymously in this document.

The collection of body fluids for diagnostic analysis has long been used in the medical, diagnostic, forensic, veterinary medical and other fields to test and monitor for the presence of specific molecules within the fluid. Results of such analyte testing can be used to diagnose medical conditions, and to measure the concentration of pharmaceutical and other drugs or toxic substances in a human or animal subject. Analyte test results can also be used to monitor appropriate levels of therapeutic agents, or for other purposes. A subject's oral fluids may be used to test for a wide variety of types of molecules whose concentration in saliva is related to the circulating concentration of those molecules or related metabolites of substances in the blood. (Malamud, D. Saliva as a diagnostic fluid. *Br. Med. J.*, 305, 207–208 (1990); Mandel, I. D. The diagnostic uses of saliva. *J. Oral Pathol. Med.*, 19, 119–125 (1990); Mandel, I. D. "Salivary Diagnosis: Promises, Promises," in Malamud, D. and Tabak, L. (eds.). *Saliva as a Diagnostic Fluid*, Vol. 694: Annals of the New York Academy of Sciences, New York: The New York Academy of Sciences (1993), pp. 1–8.)

Use of saliva as a medium for analysis is desirable since it can be obtained by noninvasive methods, unlike blood product collection methods involving trained medical personnel using venipuncture or finger-stick methods of collection. Oral fluid collection can also be done in public without requiring privacy booths, bathroom facilities, and careful subject monitoring to avoid adulteration, sample replacement, sample dilution and other problems associated with urine collections.

Previously described devices for collecting samples of oral fluids from a subject can be divided into three general categories. The first category includes devices that have an absorbent material for absorbing the oral fluid. These devices have as a common feature an absorbent material that is placed in the mouth of the subject to obtain the saliva. The absorbent material absorbs the oral fluid and is then removed from the mouth of the subject for subsequent extraction of the oral fluid from the absorbent material by any of various means.

The need for an absorbing material in these devices limits the range of substances that may be analyzed, since it has proven difficult to produce an absorptive material which will not irreversibly trap some types of analytes which may need to be analyzed. Liquid extractants have been incorporated to facilitate removal of some types of absorbed analytes. Use of these liquid extracting agents may produce additional problems of nonreproducibility and may unnecessarily dilute the sample making determination of small concentrations of some analytes in oral fluids unreliable. Added complexity involved in using these extracting agents makes the test less reliable. Extracting agents typically do not release all types of absorbed molecules equally well. Non-reversible trapping thus limits the accuracy, precision, and reliability of absorbent collection devices when semi-quantitative or quantitative analysis is necessary. (Anglebe, C., Experience with the Salivette® and some findings concerning its applicability for the determination of salivary components. *J. Clin. Biochem.*, 27, 4, 247–248 (1989).)

A second category comprises devices wherein the oral fluid is obtained by osmotic absorption. For example, U.S. Pat. No. 4,817,632 to Schramm discloses an oral fluid collection device with a semi-permeable membrane enclosing chemicals that create an osmotic pressure for drawing the oral fluid from the mouth into the chamber of the semi-permeable membrane. The sample may be later retrieved from the chamber with a needle attached to a syringe. Use of these osmotic absorption saliva collection devices is limited to lab-based situations where trained personnel are available to process the previously collected saliva samples.

These devices typically interact to nonreversibly adsorb some types of analyte molecules that may need to be measured. Sample recovery complicates the procedure. Lengthy collection times of several minutes, dilution of the saliva sample with other chemicals, and non-reproducible mixing of fluid with the hypertonic substance within the chamber cause additional problems. Obtaining acceptable accuracy and precision in subsequent semi-quantitative and quantitative diagnostic measurements has proven to be difficult with oral fluid collection devices based on osmotic collection of the sample.

The third category includes devices wherein oral fluids are collected by aspiration. For example, U.S. Pat. No. 5,050,616 to Wolff et al. includes an attachable collecting tube, a buffering chamber centrally located within the interior of the sampling device, an attachable storage tube and a means for providing suction to the sampling device. The buffering chamber has a tapered interior surface that allows the fluid to flow down into the storage tube under the force of gravity in order to preclude fluid from entering the suction means and to reduce the quantity of foam and bubbles in the sample.

South African Patent No. 934404 to Weber and van Wyk uses vacuum aspiration to affix a transparent collection wand to mouth tissue surrounding a specific salivary gland while saliva is collected by aspiration from the chosen salivary gland. Two different vacuum levels are used to hold the wand in place with an annular ring while collecting saliva at a different level of vacuum from the central portion of the collection device. The device includes a pressure gauge to indicate the vacuum level within the collection vessel and an air vent connecting the saliva collection chamber with the outside atmosphere in order to provide for the continuous flow and collection of saliva. Although this device provides for collection from a particular salivary gland, it is unsuitable for collection of saliva and oral fluids from the whole mouth.

These aspiration devices require significant interaction between the device operator and the subject and require periodic observation to determine when an adequate sample of saliva appears to have been collected. They do not assure that air bubbles are removed from the sample, which may be a frothy sample containing air and liquid, and they may not be suitable for collection of whole saliva from all regions of the mouth. Collection of saliva from a single gland requires additional time and does not provide a sample that is representative of whole saliva and may not be reflective of serum concentrations of certain analytes. None of the known devices provides for retention of volatile components of the saliva, which may need to be subsequently analyzed. Nor does any of the known devices automatically determine when an adequate volume of saliva has been collected. Accordingly, drawbacks of these known devices limit their usefulness for collecting oral fluids satisfactory for rapid, sensitive, accurate and reliable quantitative and semi-quantitative testing for diagnostic or forensic analytes.

It is therefore an object of the invention to provide an improved method and device for automatically collecting oral fluids suitable for subsequent analysis.

SUMMARY OF THE INVENTION

The method and device described provides for rapid, automatic collection of oral fluids from anywhere within the mouth without significant interaction of the instrument operator and the test subject from whom the saliva sample is collected. Automatic saliva collection prevents tampering with the collected sample by either the test subject or the instrument operator and prevents possible contamination of the operator by the subject's possibly biologically-hazardous saliva. The operator is unable to influence either the rate of collection or the size of the sample. In addition to reproducible collection of nonvolatile analytes, volatile components present in saliva, such as alcohol or acetone, can be retained for subsequent analysis of these analytes. The collected sample may be stabilized for subsequent analysis at a remote laboratory, or it may be immediately automatically processed to remove potentially interfering particulates and air bubbles and then automatically analyzed on-site in less than five (5) minutes. This permits remote site testing anywhere in real time.

DETAILED DESCRIPTION OF THE PREFERRED EMBODIMENTS

Figure 1:
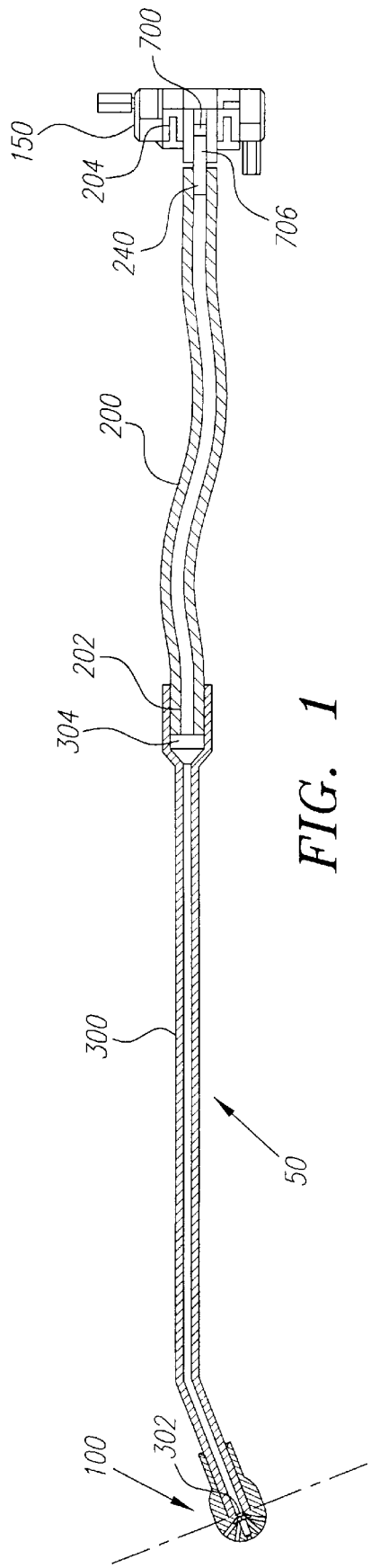
FIG. 1 is a schematic illustration of a saliva collection device.

As shown in FIG. 1, a saliva collection device (50) contains all subcomponents that may come into contact with the saliva of the subject. The device (50) is preferably made from disposable, non-toxic material that prevents subsequent contamination with possibly infectious saliva. The device is intended to be used in connection with an instrument that provides all motive devices and forces for aspirating saliva automatically from the mouth of the subject into the device. In one preferred embodiment of the device, the interface section (150) of the disposable device (50) is inserter into an instrument interface until a positive feedback signal is detected. This positive feedback signal indicates proper installation of the device (50) and automatically initiates saliva collection. When an adequate volume of saliva has been collected, the instrument stops saliva collection. This minimizes operator interaction with the saliva collection system. In other embodiments, manual initiation of the saliva collection may be employed.

The saliva collection device (50) includes a mouthpiece (100) in fluid communication with the first end (302) of a wand (300) and a flexible conduit (200). The wand (300) may be advantageously connected to the mouthpiece (100) to provide for easy maneuverability of the mouthpiece (100) within the mouth of the subject. As shown in FIG. 1, the wand (300) is a hollow rigid or semi-rigid conduit with a front or first end (302) in fluid communication with the mouthpiece (100). The back or second end (304) of the wand (300) is in fluid communication with the front or first end (202) of the flexible conduit (200).

The mouthpiece (100) may be selected from a number of different designs, yet must have a size that permits it to comfortably fit within the mouth of the subject. A smaller mouthpiece may be used with children, while a larger mouthpiece may be used when adults or large animals are to be tested. The mouthpiece is not limited to a certain size, but one preferred embodiment has a cross-sectional size from about 0.2 cm to about 1.5 cm for adult humans. The mouthpiece (100) is constructed from non-toxic, non-analyte absorbing materials, including but not limited to stainless steel, aluminum, titanium, nylon or other plastics or elastomers, or other suitable material.

Figure 3:
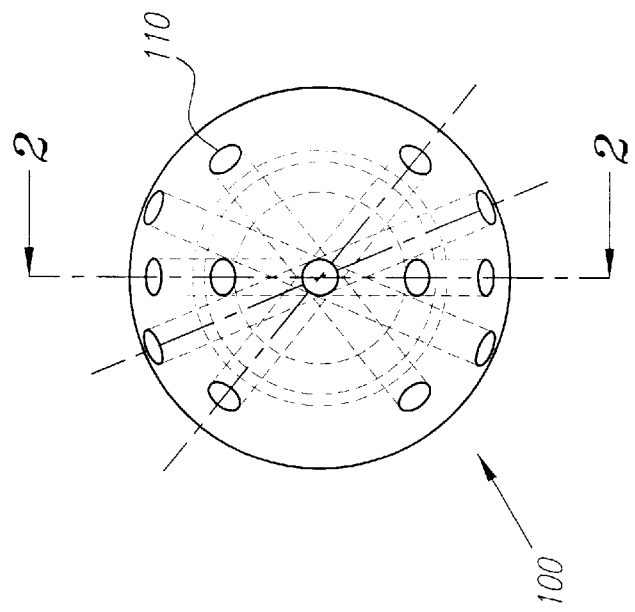
FIG. 3 is a schematic frontal view of the collection mouthpiece.
Figure 2:
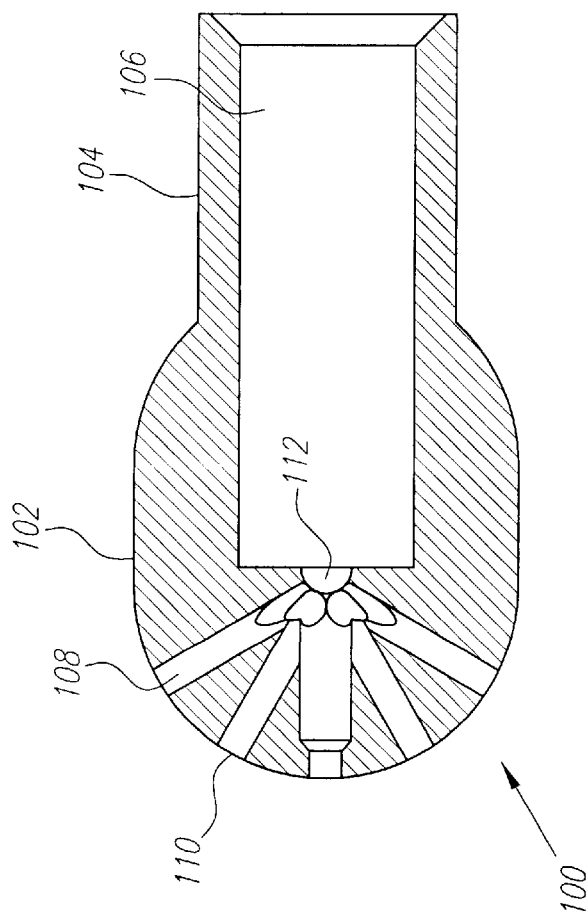
FIG. 2 is a schematic illustration of a cross section of the collection mouthpiece.

FIG. 2 is a schematic internal cross sectional view of one preferred embodiment of the mouthpiece (100). The mouthpiece (100) consists of a head (102) and a hollow shaft (104), the hollow shaft having an interior conduit (106). Ports (108) lead from orifices (110) in the surface of the head to a common manifold (112) in the center of the mouthpiece. The manifold (112) is in fluid communication with the interior conduit (106) within the hollow shaft (104). The orifices (110) and ports (108) are preferably of a small diameter, ranging from approximately 0.050 mm to about 2 mm in diameter, are either regular or irregular in size and shape, and may serve as a first filter element to prevent large solid matter from being aspirated or collected. FIG. 3 is a schematic frontal view of the collection mouthpiece showing the orifices (110) in the mouthpiece (100). An alternative mouthpiece design has 12 ports in the bottom half of the collection mouthpiece, meeting to form a common manifold in the center of the mouthpiece. A micro-porous saliva collection mouthpiece, using porous plastic, such as Porex®, may also be used.

Figure 4:
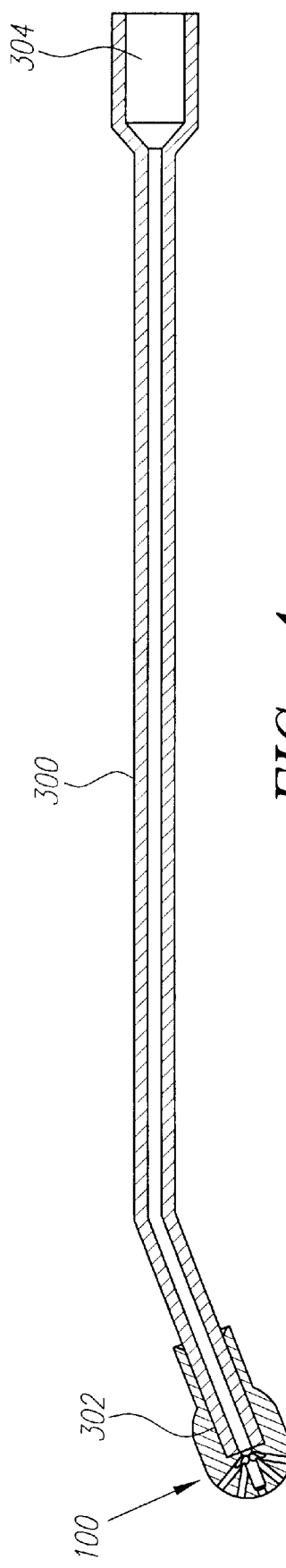
FIG. 4 is a schematic illustration of the saliva collection wand and mouthpiece.

As shown in FIG. 4, the saliva collection mouthpiece (100) is bonded, or may be molded as one piece, to the wand handle (300) to prevent separation of the mouthpiece from the wand, for example either by pulling with the hands or by a combination of biting with the teeth while pulling on the wand handle with the hand(s). For safety reasons, the wand handle (FIG. 1) and flexible tubing are of sufficient strength to prevent breakage by pulling, biting, bending, or the like.

Flow of fluid through the flexible conduit may be one or more of the following types of flow modes: "continuous", "annular", "wispy annular", "bubble", "churn", "plug" or "slug", and "stratified" (Blevins, R. D., *Applied Fluid Dynamics Handbook*, Malabar, Fla.: Krieger Publ. (1992), pp. 109–112). If only non-volatile components are to be preserved, any of these flow modes is suitable. In the event that volatile components of the saliva must be conserved, the least desirable flow modes are annular or wispy-annular which spread the fluid over the walls of the tubing giving it maximum surface area, thus rapidly evaporating volatile components from the oral fluid. It was found that plug or slug flow through the flexible conduit is desirable if volatile components are to be preserved.

Figure 5:
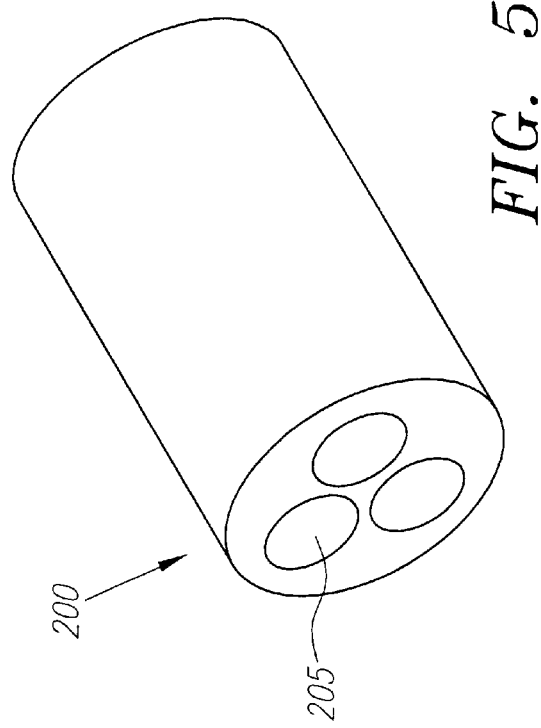
FIG. 5 is a schematic cross section view of a multi-lumen conduit.

The flexible conduit (200) should be of a length sufficient to comfortably permit the subject to place the mouthpiece in his/her mouth while the interface section of the flexible conduit (204) is fixed to the instrument. The flexible conduit may be any length but a range from about 15–60 cm (6–24 inches) has been found to be optimal. The inner surface of the flexible conduit, which contacts the saliva fluid, must be constructed from polymeric materials that are nonabsorbent to target analyte molecules. As shown in FIG. 5, the conduit may have multiple lumens (205).

The instrument contains a means of creating low pressure at the second end of the flexible conduit. This pump generates a nominal flow rate ranging between approximately 100–750, milliliters of air per minute (or standard cubic centimeters per minute—sccm) although a wider range of flow rates may be used. The lower end of the range, for rate of flow, preferably 100–750 ml/min. has been found to give the most consistent oral fluid collection results when retention of volatile components is desired. The flexible conduit (200) is fluidly coupled to the collection chamber through a one-way check valve (240). A vacuum pump generates a low pressure within the collection chamber, thus drawing the oral fluid from the mouth of the subject through the mouthpiece (100), the wand (300), the flexible conduit (200), the one-way check valve (240), and then into the collection chamber (700). The oral fluid remains at the bottom of the chamber, while the air passes through the port (706) at the top of the chamber. The vacuum pump is capable of producing maximum differential vacuum levels in the range of 50–250 torr below atmospheric pressure. Usable air flow rates are obtained in the range of 150–750 milliliters of air per minute when operated at a vacuum level ranging from 50 to 250 torr below atmospheric pressure.

Optimal oral fluid collection has been found to require transferring a sufficient amount of oral fluid, nominally 50 $\mu$L to 1000 $\mu$L, from the subject's mouth to the collection chamber (700) in the shortest amount of time possible which has been nominally found to be 30–90 seconds. However, the saliva collection should be performed with the smallest volume of airflow practicable especially when retention of volatile components from the saliva is important. Adequate vacuum levels are needed to lift the oral fluid from the mouth which may be located as much as 60 cm below the level of the saliva container. Thus the device may be used with a prone subject whose mouth may be located at a level lower than that of the saliva collection instrument.

Oral fluid must be pulled through the pores of the mouthpiece (100), through the small diameter flexible conduit (200), through the bulk air removal system/oral fluid collection chamber (700). Too small vacuum levels provide insufficient force to collect and transport the oral fluid through the resistance of the system. As the volume of oral fluid occupying various portions of the system between the mouthpiece (100) and the collection chamber (700) increases, the minimal vacuum level necessary to maintain flow through the system increases from approximately 50 to 250 torr differential vacuum. Otherwise, it has been found that oral fluid flow is interrupted. Too large a vacuum causes a greater volume of air than desirable to be transported through the system, requiring removal of greater volumes of air in the bulk air removal subsystem. Where loss of volatile components of saliva must be controlled, maintaining a constant, minimal flow of air through the system (preferably ±20% and most preferably ±5%) at all times is advantageous because volatile loss will therefore be a consistent function of time despite variable collection rates. For collection of volatiles, vacuum is preferably limited to 50–200 Torr, and the collection tube diameter is limited to 18 inches in length and 0.015–0.020 inches I.D.

A variety of methods for determining when an adequate volume of saliva has been collected may be suitable for the device and method. These include, but are not limited to, the use of: (1)pressure transducers; (2) compression of a mixture of liquid sample and confined gases into a known volume, measurement of the pressure of the confined mixture, and use of the ideal gas law to calculate the volume of gas, and thereby compute the volume of liquid that has been collected; (3) electrical conductivity of the collected liquid; (4) electrical capacitive level sensing; (5) heat-transfer level sensing; (6) using a semiconductive thermistor in self-heating mode to measure heat transfer into the liquid; (7) photoelectric level sensing; (8) damped oscillation or vibrating-element level sensing; (9) ultrasonic level sensing; (10) microwave level sensing; or any other suitable method of liquid volume determination. (Norton, H. N. "Liquid Level Sensors," *Handbook of Transducers*. Englewood Cliffs, N.J.: Prentice Hall (*1989*), Ch. 14, pp. 269–293.)

Following bulk air removal, which may occur in the collection chamber (700) or at any subsequent part of the device, any remaining air bubbles must be removed prior to analysis of analytes since saliva is of sufficient viscosity for air bubbles to become trapped. Bubble removal is not necessary if the sample is to be transported to a laboratory where subsequent diagnostic analysis will be performed.

The instrument has various interfaces that connect to the interface section of the device (50), when the interface end is inserted into the instrument. These interfaces include fittings, as needed, to permit vacuum connections, with appropriate filters or saliva barriers, to provide vacuum to the embodiment shown in FIG. 1. In this way, all components coming into contact with saliva can be handled and optionally disposed of, as a single unit, while the instrument remains entirely untouched and uncontaminated by saliva.

Thus, a novel saliva automatic collection method and device have been shown and described. Various modifications and substitutions of equivalents can of course be made without departing from the spirit and scope of the invention. The invention, therefore, should not be limited, except by the following claims and their equivalents.

What is claimed is:

1. A device for the automatic collection of oral fluids or whole saliva or saliva for medical, diagnostic, forensic, veterinary medical and other fields for testing purposes comprising:

a) a collection mouthpiece;
   b) a flexible conduit member having a first end and a second end, the first end in fluid communication with the collection mouthpiece;
   c) a saliva collection reservoir for collecting a saliva sample the collection reservoir in fluid communication with the second end of the flexible conduit member;
   d) a vacuum source in fluid communication with the saliva collection reservoir, and
   e) means for sensing a specified sample amount of saliva in the collection reservoir.

2. The device according to claim 1, wherein the collection mouthpiece is made of any nontoxic, nonabsorbent material and constructed in a size and shape to conveniently fit into the mouth of a subject to permit collection of oral fluids, whole saliva or saliva and wherein the collection mouthpiece contains at least one orifice on the surface of the collection mouthpiece and a port connecting each orifice with the interior of the collection mouthpiece.

3. The device of claim 2 wherein the at least one orifice ranges from 0.05 to 2 mm in diameter to filter out particles.

4. The device of claim 2 further including a collection manifold contained within the interior of the collection mouthpiece or in fluid contact with the collection mouthpiece and the flexible conduit.

5. An automatic oral fluid collection device according to claim 1, further including a wand having a first end connected to the collection mouthpiece, and
   a second end of the wand connected with the flexible conduit.

6. The device of claim 5 wherein the wand is hollow to permit collected saliva to flow through it or to permit the flexible conduit to pass through.

7. The device of claim 5 wherein the wand is made of any nontoxic, nonabsorbent material and is of any size and geometry that facilitates placing of the wand in the mouth for satisfactory saliva collection.

8. An automatic oral fluid collection device according to claim 1, wherein the conduit is constructed from any flexible nontoxic materials that do not absorb appreciable amounts of any desired analyte that may be contained in the collected saliva and in contact with the inner surface of the conduit.

9. The device of claim 8 wherein the inner surface of the conduit is constructed of material that permits slug or plug flow modes of liquid saliva transport through the conduit in the case where volatile analytes in the saliva must be conserved.

10. The device of claim 8 wherein the conduit has at least one interior channel for liquid transport, with each channel of the conduit having an inner diameter between 0.25 to 1.0 mm and a length of the conduit ranging from 15 to 60 cm, to reduce loss of volatile components.

11. The device of claim 8 wherein the conduit is structurally designed to prevent kinking and subsequent stoppage of fluid flow through the conduit or severing of the conduit as a result of biting with the teeth or pulling with the hands by the test subject.

12. The device of claim 8 wherein the conduit is connected at each end and bonded with sufficient means for preventing separation of the collection mouthpiece mechanism or the saliva collection reservoir from the conduit by the test subject.

13. An automatic oral fluid collection device according to claim 1, wherein the collection reservoir has a first reservoir port in fluid connection with the flexible conduit, and a second reservoir port connected to the vacuum source.

14. The device of claim 13 wherein the saliva collection reservoir has any shape and orientation that facilitates separation of bulk air from the collected saliva and facilitates indication of sample volume adequacy, and the sample collection reservoir is constructed from any material that does not absorb appreciable amounts of any target analyte present in the collected saliva.

15. An automatic oral fluid collection device according to claim 1, wherein the collection device has a vacuum source to provide a vacuum ranging between 50 to 250 torr differential, with the vacuum source in fluid connection with the saliva collection reservoir at a low-pressure end thereof and in fluid connection with the atmosphere at a high-pressure end thereof.

16. The device of claim 1 with the collection mouthpiece comprising a microporous material.

17. A method for automatically collecting oral fluids from the mouth of a subject comprising the steps of:
   a) aspirating saliva from the subject;
   b) transporting the saliva into a collection reservoir;
   c) removing from the collected sample air which may have been transported along with the saliva; and
   d) automatically detecting, via a detecting device, when an adequate amount of saliva has been collected.

18. The method according to claim 17, wherein the saliva aspiration is accomplished by a vacuum generated within the disposable saliva collection reservoir through motive force applied from an external source located outside the saliva collection reservoir.

19. An automatic oral fluid collection method according to claim 17, wherein the method of transporting the saliva into a collection reservoir is accomplished by application of a vacuum at any point in the liquid flow stream beyond the saliva collection reservoir.

20. The method of claim 17 further comprising moving the air and saliva through a fluid conduit having a diameter of 0.015–0.020 inches, to minimize annular- or wispy-annular-modes of flow and maximizing slug- or plug-flow modes, to minimize evaporation of volatile components from the collected saliva sample.

21. The method of claim 17 further comprising limiting the length of the flexible conduit between the subject and the reservoir to 18 inches, to minimize evaporation of volatile components from the collected saliva sample.

22. The method of claim 17 further comprising applying a vacuum level of 50–200 Torr to a post-collection debubbling membrane in the reservoir to collect a saliva sample while minimizing evaporation of volatile components from the collected saliva sample.

23. The method of claim 17 further comprising limiting the amount of time required to accomplish saliva sample collection to a maximum of 2 minutes, to minimize evaporation of volatile components from the collected saliva sample.

24. The method according to claim 17 further comprising the step of inserting the collection reservoir into an instrument which automatically causes saliva to be collected in the reservoir, until an adequate volume of saliva has been collected, to minimize operator interaction with the saliva collection.

25. The method of claim 17 wherein the saliva aspiration is accomplished by a vacuum generated outside the disposable saliva collection reservoir and applied to the reservoir through fluid connection to the reservoir.

26. The method of claim 17 wherein transporting the saliva is accomplished by application of a higher pressure at any point in the liquid flow stream prior to the saliva collection reservoir.

27. An automatic oral fluid sampling method for retention of volatile components of saliva comprising the steps of:
   aspirating saliva at an air flow rate of 100–200 ml/min., to reduce evaporation of volatile components from the collected saliva sample; and
   maintaining the air flow rate through the saliva collection system at a constant value ±20%, to minimize uncertainty in the amount of evaporation of volatile components from the collected saliva sample.

28. A method for collecting oral fluids from the mouth of a subject comprising the steps of:
   a) aspirating saliva from the subject;
   b) moving the saliva into a collection reservoir through a fluid conduit having a diameter of 0.015–0.020 inches, to minimize annular- or wispy-annular-modes of flow and maximizing slug- or plug-flow modes;
   c) removing from the collected sample air which may have been transported along with the saliva;
   d) indicating volume adequacy of the collected saliva sample.

29. A method for collecting oral fluids from the mouth of a subject comprising the steps of:
   a) aspirating saliva from the subject;
   b) transporting the saliva into a collection reservoir via a flexible conduit between the subject and the reservoir, the flexible conduit having a length of 18 inches or less to minimize evaporation of volatile components from the collected saliva sample;
   c) removing from the collected sample air which may have been transported along with the saliva;
   d) indicating volume adequacy of the collected saliva sample.

30. A method for collecting oral fluids from the mouth of a subject comprising the steps of:
   a) applying a vacuum level of 50–200 Torr to a post collection debubbling membrane;
   b) aspirating saliva from the subject;
   c) transporting the saliva into a collection reservoir;
   d) removing from the collected sample air which may have been transported along with the saliva;
   e) indicating volume adequacy of the collected saliva sample.

31. A method for collecting oral fluids from the mouth of a subject comprising the steps of:
   a) aspirating saliva from the subject;
   b) transporting the saliva into a collection reservoir;
   c) removing from the collected sample air which may have been transported along with the saliva;
   d) indicating volume adequacy of the collected saliva sample; and
   e) limiting the amount of time required for collecting the saliva sample collection to a maximum of 2 minutes.

32. A method for automatically collecting oral fluids from the mouth, comprising the steps of:
   a) aspirating saliva from the mouth;
   b) transporting the saliva into a collection reservoir;
   c) removing from the collected sample air which may have been transported along with the saliva;
   d) detecting, via a detecting device, when an adequate amount of saliva has been collected; and
   e) automatically stopping the aspirating when an adequate amount of saliva is detected.

* * * * *